United States Patent [19]

Rueb et al.

[11] Patent Number: 4,990,174
[45] Date of Patent: Feb. 5, 1991

[54] N-PHENYLTETRAHYDROINDAZOLE DERIVATIVES HERBICIDAL COMPOSITIONS AND USE

[75] Inventors: Lothar Rueb, Speyer; Karl Eicken, Wachenheim; Peter Plath, Frankenthal; Karl-Otto Westphalen, Speyer; Bruno Wuerzer, Otterstadt, all of Fed. Rep. of Germany

[73] Assignee: BASF Aktiengesellschaft, Ludwigshafen, Fed. Rep. of Germany

[21] Appl. No.: 462,704

[22] Filed: Jan. 9, 1990

[30] Foreign Application Priority Data

Jan. 21, 1989 [DE] Fed. Rep. of Germany ....... 3901705

[51] Int. Cl.$^5$ .................. A01N 43/56; A01N 43/84; C07D 231/56; C07D 413/10
[52] U.S. Cl. ........................................ 71/92; 544/63; 544/96; 544/140; 546/199; 548/215; 548/240; 548/372
[58] Field of Search ........................ 544/63, 96, 140; 546/199; 548/215, 240, 372; 71/92

[56] References Cited

FOREIGN PATENT DOCUMENTS 0105721 4/1984 European Pat. Off. .

Primary Examiner—Robert W. Ramsuer
Attorney, Agent, or Firm—Keil & Weinkauf

[57] ABSTRACT

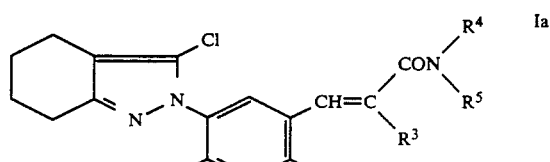

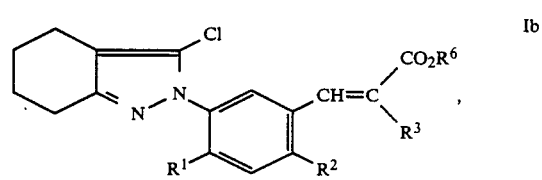

where
$R^1$ is hydrogen or fluorine,
$R^2$ is halogen,
$R^3$ is hydrogen, halogen or a $C_1$–$C_4$-alkyl,
$R^4$, $R^5$ are hydrogen, $C_1$–$C_8$-alkyl, $C_2$–$C_4$-alkyl which carries a hydroxyl, $C_1$–$C_4$-alkoxy or $C_1$–$C_4$-alkylthio radical, $C_1$–$C_6$-alkoxy, $C_3$–$C_6$-alkenyl, $C_3$–$C_6$-alkynyl, $C_3$–$C_6$-alkenyloxy and/or $C_3$–$C_6$-alkynyloxy, or together with the nitorgen atom form a 5- or 6-membered aliphatic ring in which a methylene group may be replaced by an oxygen atom, and
$R^6$ is hydrogen, $C_1$–$C_6$-alkyl which is unsubstituted or substituted by one or two $C_1$–$C_4$-alkoxy groups, or is $C_3$–$C_6$-alkenyl, $C_3$–$C_6$-alkynyl or benzyl, processes for their manufacture, and their herbicidal use.

3 Claims, No Drawings

N-PHENYLTETRAHYDROINDAZOLE DERIVATIVES HERBICIDAL COMPOSITIONS AND USE

The present invention relates to N-phenyltetrahydroindazole derivatives of the general formulae Ia and Ib

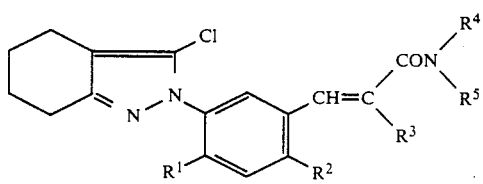

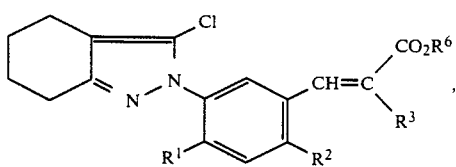

where
$R^1$ is hydrogen or fluorine,
$R^2$ is halogen,
$R^3$ is hydrogen, halogen or $C_1$-$C_4$-alkyl,
$R^4$ and $R^5$ are each hydrogen $C_1$-$C_8$-alkyl, $C_2$-$C_4$-alkyl which carry a hydroxyl, $C_1$-$C_4$-alkoxy or $C_1$-$C_4$-alkylthio group, $C_1$-$C_6$-alkoxy, $C_3$-$C_6$-alkenyl, $C_3$-$C_6$-alkynyl, $C_3$-$C_6$-alkenyloxy or $C_{3l}$ -$C_6$-alkynyloxy, or together with the nitrogen atom form a 5-membered or 6-membered aliphatic ring in which a methylene group may be replaced by an oxygen atom, and
$R^6$ is hydrogen or $C_1$-$C_6$-alkyl which is unsubstituted or substituted by one or two $C_1$-$C_4$-alkoxy groups, or is $C_3$-$C_6$-alkenyl, $C_3$-$C_6$-alkynyl or benzyl,
the formulae Ia and Ib embracing all isomeric forms of these compounds.

The invention furthermore relates to processes for the preparation of these compounds and their use as herbicides.

EP-A 105 721 discloses, inter alia, herbicidal N-phenyltetrahydroindazole derivatives I'

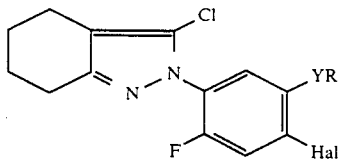

where
Hal is chlorine or bromine,
Y is oxygen or imino and
R is $C_1$-$C_4$-alkyl, $C_3$- or $C_4$-alkenyl, $C_3$- or $C_4$-alkynyl. $C_1$-$C_6$-alkoxycarbonylmethyl, $C_3$-$C_6$-cycloalkoxycarbonylmethyl or $C_1$-$C_4$-haloalkoxycarbonylmethy.

However, compounds which more effectively control undesirable plants without significantly damaging crops (selectively) when used at a low application rate are desirable, particularly for use adjacent to crops.

It is an object of the present invention to provide novel N-phenyltetrahydroindazole derivatives having improved herbicidal activity.

We have found that his object is achieved by the N-phenyltetrahydroindazole derivatives Ia and Ib defined at the outset.

We have also found processes for the preparation of the compounds Ia and Ib, the use of these compounds as herbicides, and herbicides containing these compounds.

The compounds Ia and Ib are obtained, for example, by reacting an indazolecinnamic acid derivative VII in an aprotic polar organic solvent in a conventional manner (Houben-Weyl Vol. VIII, 545, 655; X/2, 747) in the presence of a base with an amine of the formula VIII or with a compound IX.

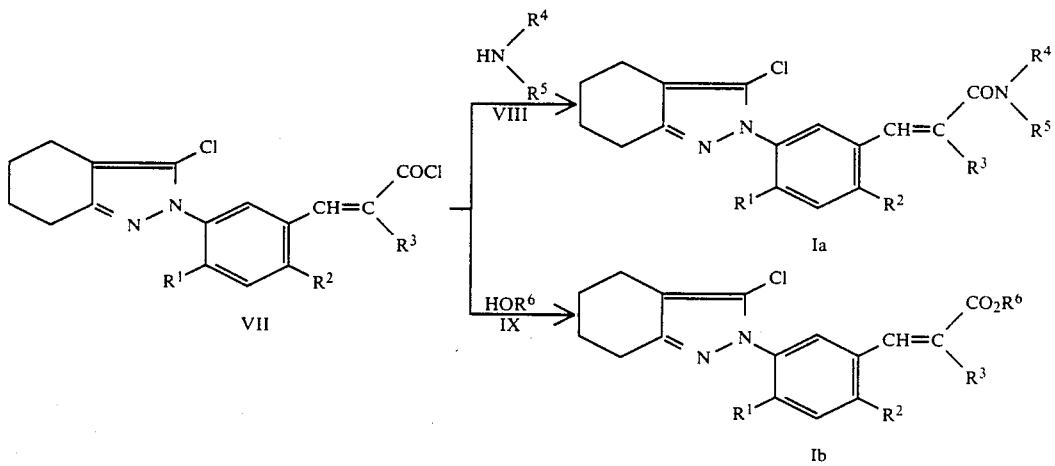

The solvents used for this reaction are mainly relatively high boiling hydrocarbons, such as xylene and toluene, carboxylic esters, such as ethyl acetate, and ethers, such as dioxane and tetrahyrofuran.

The reaction is carried out, as a rule, at from −10 to 200° C., preferably from 0 to 150° C.

Examples of suitable bases for this reaction ar tertiary amines, such as triethylamine and pyridine, or inorganic salts, such as sodium hydroxide, potassium hydroxide and potassium carbonate.

The indazolecinnamic acid derivatives VII requires for this process are obtainable in five independent reaction stages, in accordance with the reaction scheme below.

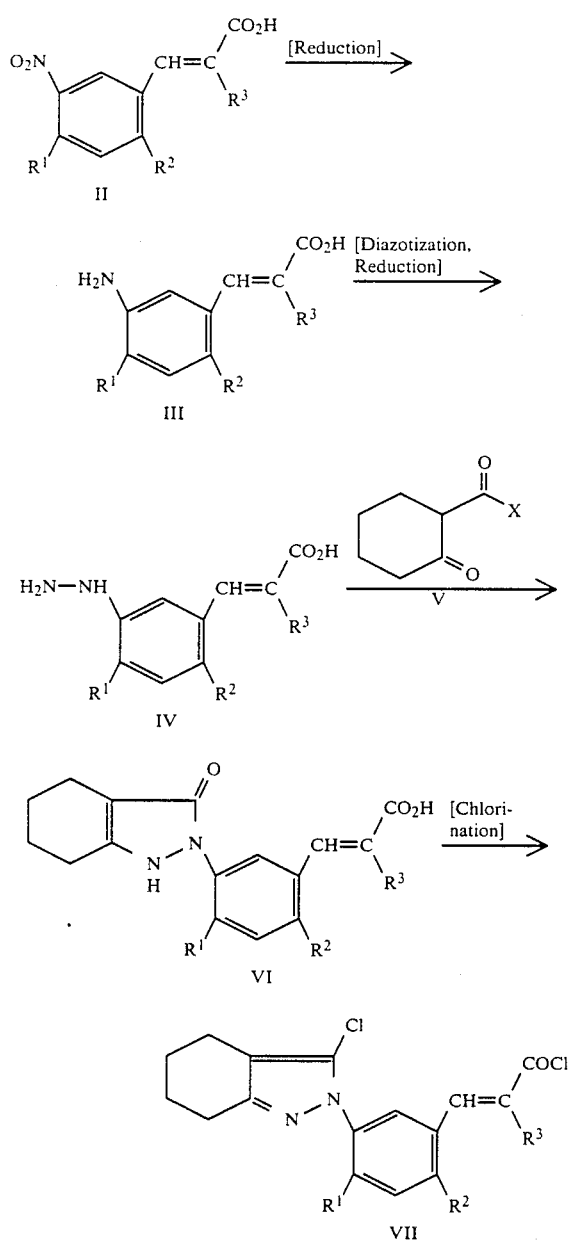

In the first stage of the reaction sequence, a nitrocinnamic acid II is reduced in a conventional manner with an inorganic compound, such as a tin(II) salt or iron, or, if $R^3$ is not halogen, by catalytic hydrogenation over a metal catalyst, such as Raney nickel, palladium or platinum, in an inert organic solvent to give the aniline derivative III.

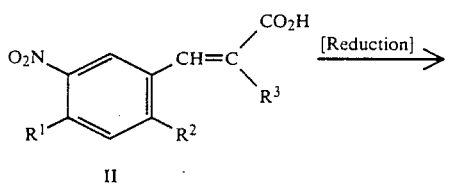

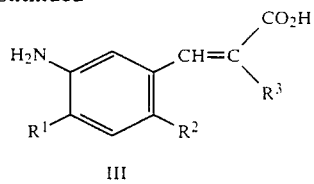

Examples of suitable solvents for the reduction with inorganic compounds are alcohols, such as methanol, ethanol and isopropanol, and lower alkanoic acids, such as formic acid, acetic acid and propionic acid, and mixtures thereof. The reaction temperatures are from 25 to 150° C., preferably from 25 to 100° C.

If the reduction is carried out with hydrogen over a metal catalyst, suitable solvents are methanol, tetrahydrofuran and glacial acetic acid or a mixture thereof, under a hydrogen pressure of from 1 to 150, preferably from 1 to 50 bar and at 25–100° C., preferably 25–70° C.

The aniline derivative III thus obtained is then diazotized in a conventional manner in an inert solvent with an inorganic or organic nitrite to give the aryldiazonium salt, which is reduced in situ with an inorganic reducing agent to give the hydrazinocinnamic acid derivative IV.

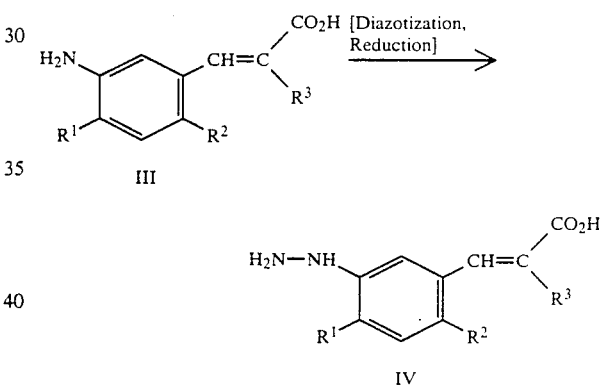

The choice of the solvent depends on the type of nitrite.

For example, inorganic nitrites, such as nitrous acid and its alkali metal and alkaline earth metal salts are preferably used in aqueous solution in the presence of mineral acids at from −30 to 50° C., preferably from −10 to 5° C.

If organic nitrites, such as amyl nitrite, are used, aprotic solvents, such as toluene, are preferred. The reaction temperature in this case is from −10 to 25° C.

The subsequent reduction is carried out in any case in situ using an inorganic reducing agent, such as a tin(II) salt, sodium dithionite or an alkali metal sulfite or bisulfite, such as sodium sulfite or sodium bisulfite, and/or with sulfur dioxide. It may be advantageous to add a solvent, such as glacial acetic acid, ethanol or toluene, for solubilization.

In the next reaction stage, the hydrazinocinnamic acid derivative IV is cyclized in a conventional manner in an inert organic solvent at up to 200° C., preferably from 25 to 150° C., with a cyclohexanone carboxylic acid derivative V to give the indazolecinnamic acid derivative VI.

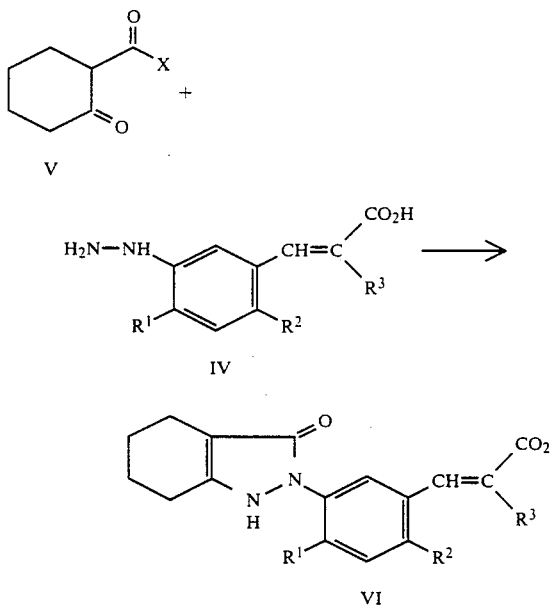

In formula V, X is a nucleophilic leaving group, such as halogen, eg. chlorine or bromine, or an alcoholate, such as methylate, ethylate, propylate, isopropylate or tosylate.

In this case, the reaction is preferably carried out in a solvent such as a lower alkanoic acid, eg. acetic acid, or in an aprotic solvent, such as toluene or xylene. If, in formula V, X is halogen, such as chlorene or bromine, it may be advantageous to carry out the reaction in the present of a tertiary amine as the base. Examples of suitable bases for this purpose are triethylamine, diisopropylethylamine, N,N-dimethylaniline, N,N-dimethyl-p-aminopyridine, pyridine, isoquinoline, N-methylpyrrolidine, N,N,N',N'-tetramethylethylenediamine, 1,5-diazabicyclo[4.3.0]non-5-ene and 1,8-diazabicyclo[5.4.0]undec-7-ene.

The indazolecinnamyl chloride VII is obtained from the indazolecinnamic acid derivative VI in a conventional manner by reaction with a chlorinating agent conventionally used in organic chemistry, in the presence or absence of an inert organic solvent and in the presence or absence of a base

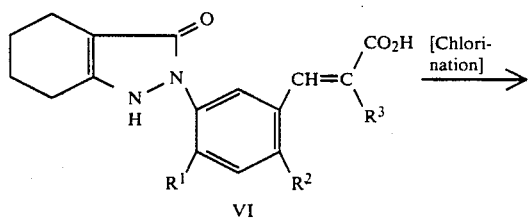

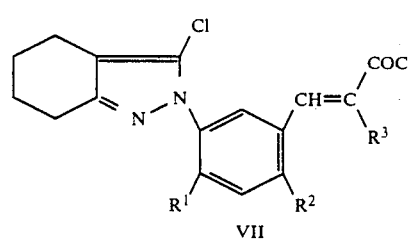

Examples of suitable chlorinating agents are oxychlorides, such as phosphorous oxytrichloride, thionyl chloride and phosgene, trichloromethyl chloroformate and chlorides, such as phosphorous trichloride, phosphorous pentachloride and sulfur tetrachloride. Phosphorous oxytrichloride is preferably used.

The reaction can be carried out at from 25 to 200° C., preferably from 60 to 160° C., in the presence or absence of a base.

Bases which are suitable for this reaction are, for example, tertiary amines, such as those stated above.

Solvents which are used here are, for example, toluene, xylene and chloroform.

However, the compounds Ia and Ib are also obtained by reacting a corresponding nitrocinnamic acid derivative IIa or IIb in a conventional manner, similarly to the reaction stages described for the nitrocinnamic acid II and shown in the scheme below.

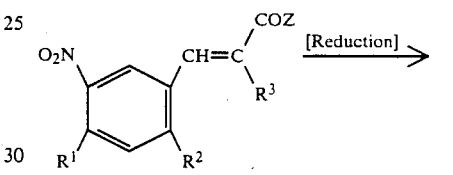

IIa (Z = NR$^4$R$^5$)
IIb (Z = OR$^6$)

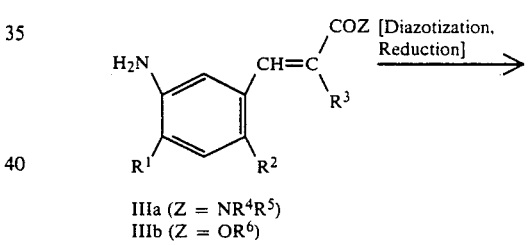

IIIa (Z = NR$^4$R$^5$)
IIIb (Z = OR$^6$)

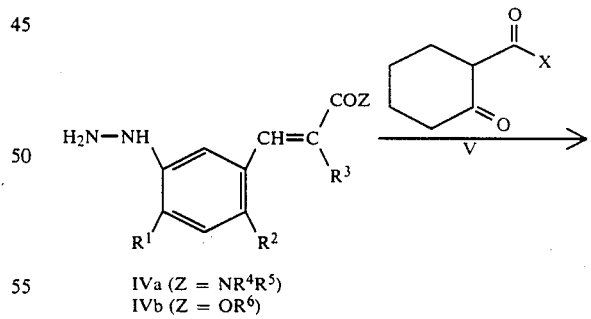

IVa (Z = NR$^4$R$^5$)
IVb (Z = OR$^6$)

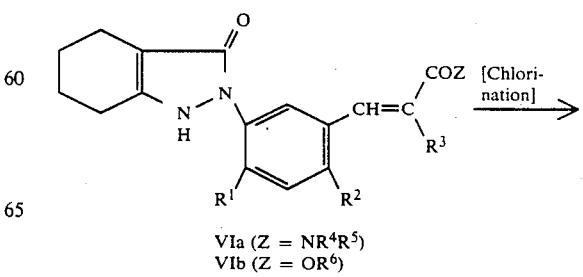

VIa (Z = NR$^4$R$^5$)
VIb (Z = OR$^6$)

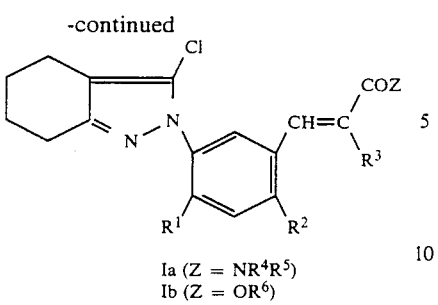

Ia (Z = NR⁴R⁵)
Ib (Z = OR⁶)

The individual stages of the synthesis are carried out in general under the conditions described above for the cinnamic acid derivative.

The reduction of the nitrocinnamic acid derivative IIa or IIb is carried out in particular in a protic polar solvent in the presence of an inorganic reducing agent at from 25 to 150° C., preferably from 40 to 100° C.

Suitable solvents here are carboxylic acids, such as acetic acid, propionic acid and isobutyric acid, and alcohols, such as methanol, ethanol and isopropanol, and mixtures thereof.

Tin(II) salts and iron are preferably used as reducing agents.

The diazotization and reduction of the aminocinnamic acid derivatives IIIa or IIIb to give the corresponding hydrazinocinnamic acid derivatives IVa or IVb, respectively, is preferably carried out in an aqueous solution in the presence of a mineral acid, such as hydrochloric acid, or a carboxylic acid, such as acetic acid, using a diazotizing agent, such as nitrous acid, sodium nitrite or potassium nitrite, and a reducing agent, such as a tin(II) salt or one of the abovementioned sulfites, at from −15 to +5° C.

The subsequent cyclization of the hydrazinocinnamic acid derivatives IVa and IVb to give the corresponding indazolecinnamic acid derivatives VIa and VIb, respectively, is preferably carried out using a cyclohexanonecarboxylic acid derivative V, in which X is alkoxy, such as methoxy, ethoxy or isopropoxy.

Particularly suitable solvents here are carboxylic acids, such as acetic acid and propionic acid. The preferred reaction temperatures are from 50 to 100° C.

Particularly suitable chlorinating agents for the conversion of the indazolecinnamic acid derivatives VIa and VIb to the N-phenyltetrahydroindazole derivatives Ia and Ib, respectively, are phosgene, phosphorous oxytrichloride and trichloromethyl chloroformate. The reaction is preferably carried out in the absence of a solvent or in toluene, xylene, dimethylformamide or chloroform as a solvent, at from 60 to 160° C.

In view of the intended use of the compounds Ia and Ib as herbicides, preferred substituents are the following radicals:

$R^1$ is hydrogen or fluorine, $R^2$ is halogen, such as fluorine, chlorine or bromine, in particular chlorine, $R^3$ is hydrogen; halogen as stated under $R^2$, in particular chlorine or bromine; alkyl, such as methyl, ethyl, propyl, 1-methylethyl, butyl, 1-methylpropyl, 2-methylpropyl and 1,1-dimethylethyl, in particular methyl or ethyl;

$R^4$ and $R^5$ are each hydrogen, alkyl, such as those stated under $R^3$ and n-pentyl, 1-methylbutyl, 2-methylbutyl, 3-methylbutyl, 1,2-dimethylpropyl, 1,1-dimethylpropyl, 2,2-dimethylpropyl, 1-ethylpropyl, n-hexyl, 1-methylpentyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,3-trimethylpropyl, 1,2,2-trimethylpropyl, 1-ethylbutyl, 2-ethylbutyl, 1-ethyl-2-methylpropyl, n-heptyl, 1-methylhexyl, 2-methylhexyl, 3-methylhexyl, 4-methylhexyl, 5-methylhexyl, 1-ethylpentyl, 2-ethylpentyl, 1-propylbutyl and octyl, and alkyl groups such as ethyl, propyl, 1-methylethyl, butyl, 1-methylpropyl, 2-methylpropyl and 1,1-dimethylethyl may be substituted by hydroxyl, alkoxy, such as methoxy, ethoxy, propoxy, 1-methylethoxy, butoxy, 1-methylpropoxy, 2-methylpropoxy, or 1,1-dimethylethoxy, or alkylthio, such as methylthio, ethylthio, propylthio, 1-methylethylthio, butylthio, 1-methylpropylthio, 2-methylpropylthio or 1,1-dimethylethylthio; alkoxy such as those stated above, and pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, hexyloxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy and 1-ethyl-2-methylpropoxy; alkenyl, such as 1-propenyl, 2-propenyl, 1-methylethenyl, 1-butenyl, 2-butenyl, 3-butenyl, 1-methyl-1-propenyl, 1-methyl-2-propenyl, 2-methyl-1-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,2-dimethyl-1-butenyl, 1,3-dimethyl-2-butenyl, 1,2-dimethyl-2-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-2-propenyl and 1-ethyl-2-methyl-2-propenyl, or a corresponding alkenyloxy group; alkynyl, such as 1-propynyl, 2-propynyl, 1-butynyl, 2-butynyl, 2-butynyl, 1-methyl-2-propynyl, 1-pentynyl, 2-pentynyl, 3-pentynyl, 4-pentynyl, 1-methyl-3-butynyl, 2-methyl-3-butynyl, 1-methyl-2-butynyl, 3-methyl-1-butynyl, 1,1-dimethyl-2-propynyl, 1-ethyl-2-propynyl, 1-hexynyl, 2-hexynyl, 3-hexynyl, 4-alkynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 3,3-dimethyl-1-butynyl, 1-ethyl-2-butynyl, 1-ethyl-4-4-butynyl, 2-ethyl-4-butynyl and 1-ethyl-1-methyl-3-propynyl, or a corresponding alkynyloxy group, or together with the nitrogen atom for ma 5-membered or 6-membered heteroaliphatic ring, such as azolidine, 1,2-oxazolidine, 1,3-oxazolidine, piperidine, perhydro-1,2-oxazine, perhydro-1,3-oxazine or morpholine;

$R^6$ is hydrogen; $C_1$-$C_6$-alkyl as stated under $R^4$ and $R^5$, in particular methyl, ethyl, propyl or isopropyl, and this alkyl group may be substituted by one or two of the $C_1$-$C_4$-alkoxy groups likewise mentioned above, alkoxyalkyl, such as methoxymethyl, 2-methoxyethyl, 2-methoxypropyl, 3-methoxypropyl, 2-methoxy-1-methylethyl, ethoxymethyl, 2-ethoxyethyl, 2-ethoxypropyl, 3-ethoxypropyl, 2-ethoxy-1-methylethyl and 1-ethoxy-1-methylethyl being particularly preferred and methoxyethyl and ethoxyethyl being very particularly preferred, or the alkenyl and alkynyl groups stated in general and in particular under $R^4$ and $R^5$, and benzyl.

Examples of very active compounds Ia and Ib are shown in Tables I and II below.

TABLE I

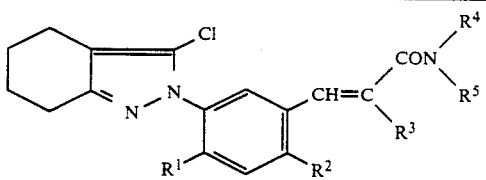

Ia

| $R^1$ | $R^2$ | $R^3$ | $R^4$ | $R^5$ |
|---|---|---|---|---|
| H | Cl | H | H | $CH_3$ |
| F | Cl | H | H | $CH_3$ |
| H | Br | H | H | $CH_3$ |
| F | Br | H | H | $CH_3$ |
| H | Cl | Cl | H | $CH_3$ |
| F | Cl | Cl | H | $CH_3$ |
| H | Br | Cl | H | $CH_3$ |
| F | Br | Cl | H | $CH_3$ |
| H | Cl | Br | H | $CH_3$ |
| F | Cl | Br | H | $CH_3$ |
| H | Br | Br | H | $CH_3$ |
| F | Br | Br | H | $CH_3$ |
| H | Cl | $CH_3$ | H | $CH_3$ |
| F | Cl | $CH_3$ | H | $CH_3$ |
| H | Br | $CH_3$ | H | $CH_3$ |
| F | Br | $CH_3$ | H | $CH_3$ |
| H | Cl | $CH_2CH_3$ | H | $CH_3$ |
| F | Cl | $CH_2CH_3$ | H | $CH_3$ |
| H | Br | $CH_2CH_3$ | H | $CH_3$ |
| F | Br | $CH_2CH_3$ | H | $CH_3$ |
| H | Cl | H | H | $CH_2CH=CH_2$ |
| F | Cl | H | H | $CH_2CH=CH_2$ |
| H | Br | H | H | $CH_2CH=CH_2$ |
| F | Br | H | H | $CH_2CH=CH_2$ |
| H | Cl | Cl | H | $CH_2CH=CH_2$ |
| F | Cl | Cl | H | $CH_2CH=CH_2$ |
| H | Br | Cl | H | $CH_2CH=CH_2$ |
| F | Br | Cl | H | $CH_2CH=CH_2$ |
| H | Cl | Br | H | $CH_2CH=CH_2$ |
| F | Cl | Br | H | $CH_2CH=CH_2$ |
| H | Br | Br | H | $CH_2CH=CH_2$ |
| F | Br | Br | H | $CH_2CH=CH_2$ |
| H | Cl | $CH_3$ | H | $CH_2CH=CH_2$ |
| F | Cl | $CH_3$ | H | $CH_2CH=CH_2$ |
| H | Br | $CH_3$ | H | $CH_2CH=CH_2$ |
| F | Br | $CH_3$ | H | $CH_2CH=CH_2$ |
| H | Cl | $CH_2CH_3$ | H | $CH_2CH=CH_2$ |
| F | Cl | $CH_2CH_3$ | H | $CH_2CH=CH_2$ |
| H | Br | $CH_2CH_3$ | H | $CH_2CH=CH_2$ |
| F | Br | $CH_2CH_3$ | H | $CH_2CH=CH_2$ |
| H | Cl | H | H | $CH_2C\equiv CH$ |
| F | Cl | H | H | $CH_2C\equiv CH$ |
| H | Br | H | H | $CH_2C\equiv CH$ |
| F | Br | H | H | $CH_2C\equiv CH$ |
| H | Cl | Cl | H | $CH_2C\equiv CH$ |
| F | Cl | Cl | H | $CH_2C\equiv CH$ |

TABLE I-continued

| $R^1$ | $R^2$ | $R^3$ | $R^4$ | $R^5$ |
|---|---|---|---|---|
| H | Br | Cl | H | $CH_2C\equiv CH$ |
| F | Br | Cl | H | $CH_2C\equiv CH$ |
| H | Cl | Br | H | $CH_2C\equiv CH$ |
| F | Cl | Br | H | $CH_2C\equiv CH$ |
| H | Br | Br | H | $CH_2C\equiv CH$ |
| F | Br | Br | H | $CH_2C\equiv CH$ |
| H | Cl | $CH_3$ | H | $CH_2C\equiv CH$ |
| F | Cl | $CH_3$ | H | $CH_2C\equiv CH$ |
| H | Br | $CH_3$ | H | $CH_2C\equiv CH$ |
| F | Br | $CH_3$ | H | $CH_2C\equiv CH$ |
| H | Cl | $CH_2CH_3$ | H | $CH_2C\equiv CH$ |
| F | Cl | $CH_2CH_3$ | H | $CH_2C\equiv CH$ |
| H | Br | $CH_2CH_3$ | H | $CH_2C\equiv CH$ |
| F | Br | $CH_2CH_3$ | H | $CH_2C\equiv CH$ |
| H | Cl | H | H | $(CH_2)_2OCH_3$ |
| F | Cl | H | H | $(CH_2)_2OCH_3$ |
| H | Br | H | H | $(CH_2)_2OCH_3$ |
| F | Br | H | H | $(CH_2)_2OCH_3$ |
| H | Cl | Cl | H | $(CH_2)_2OCH_3$ |
| F | Cl | Cl | H | $(CH_2)_2OCH_3$ |
| H | Br | Cl | H | $(CH_2)_2OCH_3$ |
| F | Br | Cl | H | $(CH_2)_2OCH_3$ |
| H | Cl | Br | H | $(CH_2)_2OCH_3$ |
| F | Cl | Br | H | $(CH_2)_2OCH_3$ |
| H | Br | Br | H | $(CH_2)_2OCH_3$ |
| F | Br | Br | H | $(CH_2)_2OCH_3$ |
| H | Cl | $CH_3$ | H | $(CH_2)_2OCH_3$ |
| F | Cl | $CH_3$ | H | $(CH_2)_2OCH_3$ |
| H | Br | $CH_3$ | H | $(CH_2)_2OCH_3$ |
| F | Br | $CH_3$ | H | $(CH_2)_2OCH_3$ |
| H | Cl | $CH_2CH_3$ | H | $(CH_2)_2OCH_3$ |
| F | Cl | $CH_2CH_3$ | H | $(CH_2)_2OCH_3$ |
| H | Br | $CH_2CH_3$ | H | $(CH_2)_2OCH_3$ |
| F | Br | $CH_2CH_3$ | H | $(CH_2)_2OCH_3$ |
| H | Cl | H | H | $OCH_2CH_3$ |
| F | Cl | H | H | $OCH_2CH_3$ |
| H | Br | H | H | $OCH_2CH_3$ |
| F | Br | H | H | $OCH_2CH_3$ |
| H | Cl | Cl | H | $OCH_2CH_3$ |
| F | Cl | Cl | H | $OCH_2CH_3$ |
| H | Br | Cl | H | $OCH_2CH_3$ |
| F | Br | Cl | H | $OCH_2CH_3$ |
| H | Cl | Br | H | $OCH_2CH_3$ |
| F | Cl | Br | H | $OCH_2CH_3$ |
| H | Br | Br | H | $OCH_2CH_3$ |
| F | Br | Br | H | $OCH_2CH_3$ |
| H | Cl | $CH_3$ | H | $OCH_2CH_3$ |
| F | Cl | $CH_3$ | H | $OCH_2CH_3$ |
| H | Br | $CH_3$ | H | $OCH_2CH_3$ |
| F | Br | $CH_3$ | H | $OCH_2CH_3$ |
| H | Cl | $CH_2CH_3$ | H | $OCH_2CH_3$ |
| F | Cl | $CH_2CH_3$ | H | $OCH_2CH_3$ |
| H | Br | $CH_2CH_3$ | H | $OCH_2CH_3$ |
| F | Br | $CH_2CH_3$ | H | $OCH_2CH_3$ |
| H | Cl | H | H | $OCH_2CH=CH_2$ |
| F | Cl | H | H | $OCH_2CH=CH_2$ |
| H | Br | H | H | $OCH_2CH=CH_2$ |
| F | Br | H | H | $OCH_2CH=CH_2$ |
| H | Cl | Cl | H | $OCH_2CH=CH_2$ |
| F | Cl | Cl | H | $OCH_2CH=CH_2$ |
| H | Br | Cl | H | $OCH_2CH=CH_2$ |
| F | Br | Cl | H | $OCH_2CH=CH_2$ |
| H | Cl | Br | H | $OCH_2CH=CH_2$ |
| F | Cl | Br | H | $OCH_2CH=CH_2$ |
| H | Br | Br | H | $OCH_2CH=CH_2$ |
| F | Br | Br | H | $OCH_2CH=CH_2$ |
| H | Cl | $CH_3$ | H | $OCH_2CH=CH_2$ |
| F | Cl | $CH_3$ | H | $OCH_2CH=CH_2$ |
| H | Br | $CH_3$ | H | $OCH_2CH=CH_2$ |
| F | Br | $CH_3$ | H | $OCH_2CH=CH_2$ |
| H | Cl | $CH_2CH_3$ | H | $OCH_2CH=CH_2$ |
| F | Cl | $CH_2CH_3$ | H | $OCH_2CH=CH_2$ |
| H | Br | $CH_2CH_3$ | H | $OCH_2CH=CH_2$ |
| F | Br | $CH_2CH_3$ | H | $OCH_2CH=CH_2$ |
| H | Cl | H | H | $OCH_2C\equiv CH$ |
| F | Cl | H | H | $OCH_2C\equiv CH$ |
| H | Br | H | H | $OCH_2C\equiv CH$ |
| F | Br | H | H | $OCH_2C\equiv CH$ |
| H | Cl | Cl | H | $OCH_2C\equiv CH$ |
| F | Cl | Cl | H | $OCH_2C\equiv CH$ |
| H | Br | Cl | H | $OCH_2C\equiv CH$ |
| F | Br | Cl | H | $OCH_2C\equiv CH$ |

TABLE I-continued

| | | | | |
|---|---|---|---|---|
| H | Cl | Br | H | OCH$_2$C≡CH |
| F | Cl | Br | H | OCH$_2$C≡CH |
| H | Br | Br | H | OCH$_2$C≡CH |
| F | Br | Br | H | OCH$_2$C≡CH |
| H | Cl | CH$_3$ | H | OCH$_2$C≡CH |
| F | Cl | CH$_3$ | H | OCH$_2$C≡CH |
| H | Br | CH$_3$ | H | OCH$_2$C≡CH |
| F | Br | CH$_3$ | H | OCH$_2$C≡CH |
| H | Cl | CH$_2$CH$_3$ | H | OCH$_2$C≡CH |
| F | Cl | CH$_2$CH$_3$ | H | OCH$_2$C≡CH |
| H | Br | CH$_2$CH$_3$ | H | OCH$_2$C≡CH |
| F | Br | CH$_2$CH$_3$ | H | OCH$_2$C≡CH |
| H | Cl | H | CH$_3$ | CH$_3$ |
| F | Cl | H | CH$_3$ | CH$_3$ |
| H | Cl | Cl | CH$_3$ | CH$_3$ |
| F | Cl | Cl | CH$_3$ | CH$_3$ |
| H | Cl | Br | CH$_3$ | CH$_3$ |
| F | Cl | Br | CH$_3$ | CH$_3$ |
| H | Cl | CH$_3$ | CH$_3$ | CH$_3$ |
| F | Cl | CH$_3$ | CH$_3$ | CH$_3$ |
| H | Cl | CH$_2$CH$_3$ | CH$_3$ | CH$_3$ |
| F | Cl | CH$_2$CH$_3$ | CH$_3$ | CH$_3$ |
| H | Cl | H | CH$_3$ | CH(CH$_3$)$_2$ |
| F | Cl | H | CH$_3$ | CH(CH$_3$)$_2$ |
| H | Cl | Cl | CH$_3$ | CH(CH$_3$)$_2$ |
| F | Cl | Cl | CH$_3$ | CH(CH$_3$)$_2$ |
| H | Cl | Br | CH$_3$ | CH(CH$_3$)$_2$ |
| F | Cl | Br | CH$_3$ | CH(CH$_3$)$_2$ |
| H | Cl | CH$_3$ | CH$_3$ | CH(CH$_3$)$_2$ |
| F | Cl | CH$_3$ | CH$_3$ | CH(CH$_3$)$_2$ |
| H | Cl | CH$_2$CH$_3$ | CH$_3$ | CH(CH$_3$)$_2$ |
| F | Cl | CH$_2$CH$_3$ | CH$_3$ | CH(CH$_3$)$_2$ |
| H | Cl | H | CH$_3$ | CH$_2$CH=CH$_2$ |
| F | Cl | H | CH$_3$ | CH$_2$CH=CH$_2$ |
| H | Cl | Cl | CH$_3$ | CH$_2$CH=CH$_2$ |
| F | Cl | Cl | CH$_3$ | CH$_2$CH=CH$_2$ |
| H | Cl | Br | CH$_3$ | CH$_2$CH=CH$_2$ |
| F | Cl | Br | CH$_3$ | CH$_2$CH=CH$_2$ |
| H | Cl | CH$_3$ | CH$_3$ | CH$_2$CH=CH$_2$ |
| F | Cl | CH$_3$ | CH$_3$ | CH$_2$CH=CH$_2$ |
| H | Cl | CH$_2$CH$_3$ | CH$_3$ | CH$_2$CH=CH$_2$ |
| F | Cl | CH$_2$CH$_3$ | CH$_3$ | CH$_2$CH=CH$_2$ |
| H | Cl | H | CH$_3$ | CH$_2$C≡CH |
| F | Cl | H | CH$_3$ | CH$_2$C≡CH |
| H | Cl | Cl | CH$_3$ | CH$_2$C≡CH |
| F | Cl | Cl | CH$_3$ | CH$_2$C≡CH |
| H | Cl | Br | CH$_3$ | CH$_2$C≡CH |
| F | Cl | Br | CH$_3$ | CH$_2$C≡CH |
| H | Cl | CH$_3$ | CH$_3$ | CH$_2$C≡CH |
| F | Cl | CH$_3$ | CH$_3$ | CH$_2$C≡CH |
| H | Cl | CH$_2$CH$_3$ | CH$_3$ | CH$_2$C≡CH |
| F | Cl | CH$_2$CH$_3$ | CH$_3$ | CH$_2$C≡CH |
| H | Cl | H | CH$_3$ | OCH$_3$ |
| F | Cl | H | CH$_3$ | OCH$_3$ |
| H | Cl | Cl | CH$_3$ | OCH$_3$ |
| F | Cl | Cl | CH$_3$ | OCH$_3$ |
| H | Cl | Br | CH$_3$ | OCH$_3$ |
| F | Cl | Br | CH$_3$ | OCH$_3$ |
| H | Cl | CH$_3$ | CH$_3$ | OCH$_3$ |
| F | Cl | CH$_3$ | CH$_3$ | OCH$_3$ |
| H | Cl | CH$_2$CH$_3$ | CH$_3$ | OCH$_3$ |
| F | Cl | CH$_2$CH$_3$ | CH$_3$ | OCH$_3$ |
| H | Cl | H | CH$_3$ | OCH$_2$CH=CH$_2$ |
| F | Cl | H | CH$_3$ | OCH$_2$CH=CH$_2$ |
| H | Cl | Cl | CH$_3$ | OCH$_2$CH=CH$_2$ |
| F | Cl | Cl | CH$_3$ | OCH$_2$CH=CH$_2$ |
| H | Cl | Br | CH$_3$ | OCH$_2$CH=CH$_2$ |
| F | Cl | Br | CH$_3$ | OCH$_2$CH=CH$_2$ |
| H | Cl | CH$_3$ | CH$_3$ | OCH$_2$CH=CH$_2$ |
| F | Cl | CH$_3$ | CH$_3$ | OCH$_2$CH=CH$_2$ |
| H | Cl | CH$_2$CH$_3$ | CH$_3$ | OCH$_2$CH=CH$_2$ |
| F | Cl | CH$_2$CH$_3$ | CH$_3$ | OCH$_2$CH=CH$_2$ |
| H | Cl | H | CH$_3$ | OCH$_2$C≡CH |
| F | Cl | H | CH$_3$ | OCH$_2$C≡CH |
| H | Cl | Cl | CH$_3$ | OCH$_2$C≡CH |
| F | Cl | Cl | CH$_3$ | OCH$_2$C≡CH |
| H | Cl | Br | CH$_3$ | OCH$_2$C≡CH |
| F | Cl | Br | CH$_3$ | OCH$_2$C≡CH |
| H | Cl | CH$_3$ | CH$_3$ | OCH$_2$C≡CH |
| F | Cl | CH$_3$ | CH$_3$ | OCH$_2$C≡CH |
| H | Cl | CH$_2$CH$_3$ | CH$_3$ | OCH$_2$C≡CH |
| F | Cl | CH$_2$CH$_3$ | CH$_3$ | OCH$_2$C≡CH |
| H | Cl | H | CH$_3$ | (CH$_2$)$_2$OCH$_3$ |
| F | Cl | H | CH$_3$ | (CH$_2$)$_2$OCH$_3$ |
| H | Cl | Cl | CH$_3$ | (CH$_2$)$_2$OCH$_3$ |
| F | Cl | Cl | CH$_3$ | (CH$_2$)$_2$OCH$_3$ |
| H | Cl | Br | CH$_3$ | (CH$_2$)$_2$OCH$_3$ |
| F | Cl | Br | CH$_3$ | (CH$_2$)$_2$OCH$_3$ |
| H | Cl | CH$_3$ | CH$_3$ | (CH$_2$)$_2$OCH$_3$ |
| F | Cl | CH$_3$ | CH$_3$ | (CH$_2$)$_2$OCH$_3$ |
| H | Cl | CH$_2$CH$_3$ | CH$_3$ | (CH$_2$)$_2$OCH$_3$ |
| F | Cl | CH$_2$CH$_3$ | CH$_3$ | (CH$_2$)$_2$OCH$_3$ |
| H | Cl | H | CH$_2$CH$_3$ | CH$_2$CH$_3$ |
| F | Cl | H | CH$_2$CH$_3$ | CH$_2$CH$_3$ |
| H | Cl | Cl | CH$_2$CH$_3$ | CH$_2$CH$_3$ |
| F | Cl | Cl | CH$_2$CH$_3$ | CH$_2$CH$_3$ |
| H | Cl | Br | CH$_2$CH$_3$ | CH$_2$CH$_3$ |
| F | Cl | Br | CH$_2$CH$_3$ | CH$_2$CH$_3$ |
| H | Cl | CH$_3$ | CH$_2$CH$_3$ | CH$_2$CH$_3$ |
| F | Cl | CH$_3$ | CH$_2$CH$_3$ | CH$_2$CH$_3$ |
| H | Cl | CH$_2$CH$_3$ | CH$_2$CH$_3$ | CH$_2$CH$_3$ |
| F | Cl | CH$_2$CH$_3$ | CH$_2$CH$_3$ | CH$_2$CH$_3$ |
| H | Cl | H | CH(CH$_3$)$_2$ | CH(CH$_3$)$_2$ |
| F | Cl | H | CH(CH$_3$)$_2$ | CH(CH$_3$)$_2$ |
| H | Cl | Cl | CH(CH$_3$)$_2$ | CH(CH$_3$)$_2$ |
| F | Cl | Cl | CH(CH$_3$)$_2$ | CH(CH$_3$)$_2$ |
| H | Cl | Br | CH(CH$_3$)$_2$ | CH(CH$_3$)$_2$ |
| F | Cl | Br | CH(CH$_3$)$_2$ | CH(CH$_3$)$_2$ |
| H | Cl | CH$_3$ | CH(CH$_3$)$_2$ | CH(CH$_3$)$_2$ |
| F | Cl | CH$_3$ | CH(CH$_3$)$_2$ | CH(CH$_3$)$_2$ |
| H | Cl | CH$_2$CH$_3$ | CH(CH$_3$)$_2$ | CH(CH$_3$)$_2$ |
| F | Cl | CH$_2$CH$_3$ | CH(CH$_3$)$_2$ | CH(CH$_3$)$_2$ |
| H | Cl | H | CH$_2$CH=CH$_2$ | CH$_2$CH=CH$_2$ |
| F | Cl | H | CH$_2$CH=CH$_2$ | CH$_2$CH=CH$_2$ |
| H | Cl | Cl | CH$_2$CH=CH$_2$ | CH$_2$CH=CH$_2$ |
| F | Cl | Cl | CH$_2$CH=CH$_2$ | CH$_2$CH=CH$_2$ |
| H | Cl | Br | CH$_2$CH=CH$_2$ | CH$_2$CH=CH$_2$ |
| F | Cl | Br | CH$_2$CH=CH$_2$ | CH$_2$CH=CH$_2$ |
| H | Cl | CH$_3$ | CH$_2$CH=CH$_2$ | CH$_2$CH=CH$_2$ |
| F | Cl | CH$_3$ | CH$_2$CH=CH$_2$ | CH$_2$CH=CH$_2$ |
| H | Cl | CH$_2$CH$_3$ | CH$_2$CH=CH$_2$ | CH$_2$CH=CH$_2$ |
| F | Cl | CH$_2$CH$_3$ | CH$_2$CH=CH$_2$ | CH$_2$CH=CH$_2$ |
| H | Cl | H | (CH$_2$)$_2$OCH$_3$ | (CH$_2$)$_2$OCH$_3$ |
| F | Cl | H | (CH$_2$)$_2$OCH$_3$ | (CH$_2$)$_2$OCH$_3$ |
| H | Cl | Cl | (CH$_2$)$_2$OCH$_3$ | (CH$_2$)$_2$OCH$_3$ |
| F | Cl | Cl | (CH$_2$)$_2$OCH$_3$ | (CH$_2$)$_2$OCH$_3$ |
| H | Cl | Br | (CH$_2$)$_2$OCH$_3$ | (CH$_2$)$_2$OCH$_3$ |
| F | Cl | Br | (CH$_2$)$_2$OCH$_3$ | (CH$_2$)$_2$OCH$_3$ |
| H | Cl | CH$_3$ | (CH$_2$)$_2$OCH$_3$ | (CH$_2$)$_2$OCH$_3$ |
| F | Cl | CH$_3$ | (CH$_2$)$_2$OCH$_3$ | (CH$_2$)$_2$OCH$_3$ |
| H | Cl | CH$_2$CH$_3$ | (CH$_2$)$_2$OCH$_3$ | (CH$_2$)$_2$OCH$_3$ |
| F | Cl | CH$_2$CH$_3$ | (CH$_2$)$_2$OCH$_3$ | (CH$_2$)$_2$OCH$_3$ |
| H | Cl | H | (CH$_2$)$_2$OCH$_3$ | CH$_2$CH=CH$_2$ |
| F | Cl | H | (CH$_2$)$_2$OCH$_3$ | CH$_2$CH=CH$_2$ |
| H | Cl | Cl | (CH$_2$)$_2$OCH$_3$ | CH$_2$CH=CH$_2$ |
| F | Cl | Cl | (CH$_2$)$_2$OCH$_3$ | CH$_2$CH=CH$_2$ |
| H | Cl | Br | (CH$_2$)$_2$OCH$_3$ | CH$_2$CH=CH$_2$ |
| F | Cl | Br | (CH$_2$)$_2$OCH$_3$ | CH$_2$CH=CH$_2$ |
| H | Cl | CH$_3$ | (CH$_2$)$_2$OCH$_3$ | CH$_2$CH=CH$_2$ |
| F | Cl | CH$_3$ | (CH$_2$)$_2$OCH$_3$ | CH$_2$CH=CH$_2$ |
| H | Cl | CH$_2$CH$_3$ | (CH$_2$)$_2$OCH$_3$ | CH$_2$CH=CH$_2$ |
| F | Cl | CH$_2$CH$_3$ | (CH$_2$)$_2$OCH$_3$ | CH$_2$CH=CH$_2$ |
| H | Cl | H | (CH$_2$)$_2$OCH$_3$ | CH$_2$CH≡CH |
| F | Cl | H | (CH$_2$)$_2$OCH$_3$ | CH$_2$CH≡CH |
| H | Cl | Cl | (CH$_2$)$_2$OCH$_3$ | CH$_2$CH≡CH |
| F | Cl | Cl | (CH$_2$)$_2$OCH$_3$ | CH$_2$CH≡CH |
| H | Cl | Br | (CH$_2$)$_2$OCH$_3$ | CH$_2$CH≡CH |
| F | Cl | Br | (CH$_2$)$_2$OCH$_3$ | CH$_2$CH≡CH |
| H | Cl | CH$_3$ | (CH$_2$)$_2$OCH$_3$ | CH$_2$CH≡CH |
| F | Cl | CH$_3$ | (CH$_2$)$_2$OCH$_3$ | CH$_2$CH≡CH |
| H | Cl | CH$_2$CH$_3$ | (CH$_2$)$_2$OCH$_3$ | CH$_2$CH≡CH |
| F | Cl | CH$_2$CH$_3$ | (CH$_2$)$_2$OCH$_3$ | CH$_2$CH≡CH |
| H | Cl | H | (CH$_2$)$_2$OCH$_3$ | OCH$_3$ |
| F | Cl | H | (CH$_2$)$_2$OCH$_3$ | OCH$_3$ |
| H | Cl | Cl | (CH$_2$)$_2$OCH$_3$ | OCH$_3$ |
| F | Cl | Cl | (CH$_2$)$_2$OCH$_3$ | OCH$_3$ |
| H | Cl | Br | (CH$_2$)$_2$OCH$_3$ | OCH$_3$ |
| F | Cl | Br | (CH$_2$)$_2$OCH$_3$ | OCH$_3$ |
| H | Cl | CH$_3$ | (CH$_2$)$_2$OCH$_3$ | OCH$_3$ |
| F | Cl | CH$_3$ | (CH$_2$)$_2$OCH$_3$ | OCH$_3$ |
| H | Cl | CH$_2$CH$_3$ | (CH$_2$)$_2$OCH$_3$ | OCH$_3$ |
| F | Cl | CH$_2$CH$_3$ | (CH$_2$)$_2$OCH$_3$ | OCH$_3$ |
| H | Cl | H | (CH$_2$)$_2$OCH$_3$ | OCH$_2$CH=CH$_2$ |
| F | Cl | H | (CH$_2$)$_2$OCH$_3$ | OCH$_2$CH=CH$_2$ |

TABLE I-continued

| R¹ | R² | R³ | R⁴ | R⁵ |
|---|---|---|---|---|
| H | Cl | Cl | (CH₂)₂OCH₃ | OCH₂CH=CH₂ |
| F | Cl | Cl | (CH₂)₂OCH₃ | OCH₂CH=CH₂ |
| H | Cl | Br | (CH₂)₂OCH₃ | OCH₂CH=CH₂ |
| F | Cl | Br | (CH₂)₂OCH₃ | OCH₂CH=CH₂ |
| H | Cl | CH₃ | (CH₂)₂OCH₃ | OCH₂CH=CH₂ |
| F | Cl | CH₃ | (CH₂)₂OCH₃ | OCH₂CH=CH₂ |
| H | Cl | CH₂CH₃ | (CH₂)₂OCH₃ | OCH₂CH=CH₂ |
| F | Cl | CH₂CH₃ | (CH₂)₂OCH₃ | OCH₂CH=CH₂ |
| H | Cl | H | (CH₂)₂OCH₃ | OCH₂C≡CH |
| F | Cl | H | (CH₂)₂OCH₃ | OCH₂C≡CH |
| H | Cl | Cl | (CH₂)₂OCH₃ | OCH₂C≡CH |
| F | Cl | Cl | (CH₂)₂OCH₃ | OCH₂C≡CH |
| H | Cl | Br | (CH₂)₂OCH₃ | OCH₂C≡CH |
| F | Cl | Br | (CH₂)₂OCH₃ | OCH₂C≡CH |
| H | Cl | CH₃ | (CH₂)₂OCH₃ | OCH₂C≡CH |
| F | Cl | CH₃ | (CH₂)₂OCH₃ | OCH₂C≡CH |
| H | Cl | CH₂CH₃ | (CH₂)₂OCH₃ | OCH₂C≡CH |
| F | Cl | CH₂CH₃ | (CH₂)₂OCH₃ | OCH₂C≡CH |
| H | Cl | H | CH₂CH=CH₂ | OCH₃ |
| F | Cl | H | CH₂CH=CH₂ | OCH₃ |
| H | Cl | Cl | CH₂CH=CH₂ | OCH₃ |
| F | Cl | Cl | CH₂CH=CH₂ | OCH₃ |
| H | Cl | Br | CH₂CH=CH₂ | OCH₃ |
| F | Cl | Br | CH₂CH=CH₂ | OCH₃ |
| H | Cl | CH₃ | CH₂CH=CH₂ | OCH₃ |
| F | Cl | CH₃ | CH₂CH=CH₂ | OCH₃ |
| H | Cl | CH₂CH₃ | CH₂CH=CH₂ | OCH₃ |
| F | Cl | CH₂CH₃ | CH₂CH=CH₂ | OCH₃ |
| H | Cl | H | CH₂C≡CH | OCH₃ |
| F | Cl | H | CH₂C≡CH | OCH₃ |
| H | Cl | Cl | CH₂C≡CH | OCH₃ |
| F | Cl | Cl | CH₂C≡CH | OCH₃ |
| H | Cl | Br | CH₂C≡CH | OCH₃ |
| F | Cl | Br | CH₂C≡CH | OCH₃ |
| H | Cl | CH₃ | CH₂C≡CH | OCH₃ |
| F | Cl | CH₃ | CH₂C≡CH | OCH₃ |
| H | Cl | CH₂CH₃ | CH₂C≡CH | OCH₃ |
| F | Cl | CH₂CH₃ | CH₂C≡CH | OCH₃ |
| H | Cl | H | —CH₂CH₂CH₂CH₂— | |
| F | Cl | H | —CH₂CH₂CH₂CH₂— | |
| H | Cl | Cl | —CH₂CH₂CH₂CH₂— | |
| F | Cl | Cl | —CH₂CH₂CH₂CH₂— | |
| H | Cl | Br | —CH₂CH₂CH₂CH₂— | |
| F | Cl | Br | —CH₂CH₂CH₂CH₂— | |
| H | Cl | CH₃ | —CH₂CH₂CH₂CH₂— | |
| F | Cl | CH₃ | —CH₂CH₂CH₂CH₂— | |
| H | Cl | CH₂CH₃ | —CH₂CH₂CH₂CH₂— | |
| F | Cl | CH₂CH₃ | —CH₂CH₂CH₂CH₂— | |
| H | Cl | H | —CH₂CH₂CH₂CH₂CH₂— | |
| F | Cl | H | —CH₂CH₂CH₂CH₂CH₂— | |
| H | Cl | Cl | —CH₂CH₂CH₂CH₂CH₂— | |
| F | Cl | Cl | —CH₂CH₂CH₂CH₂CH₂— | |
| H | Cl | Br | —CH₂CH₂CH₂CH₂CH₂— | |
| F | Cl | Br | —CH₂CH₂CH₂CH₂CH₂— | |
| H | Cl | CH₃ | —CH₂CH₂CH₂CH₂CH₂— | |
| F | Cl | CH₃ | —CH₂CH₂CH₂CH₂CH₂— | |
| H | Cl | CH₂CH₃ | —CH₂CH₂CH₂CH₂CH₂— | |
| F | Cl | CH₂CH₃ | —CH₂CH₂CH₂CH₂CH₂— | |
| H | Cl | H | —OCH₂CH₂CH₂— | |
| F | Cl | H | —OCH₂CH₂CH₂— | |
| H | Cl | Cl | —OCH₂CH₂CH₂— | |
| F | Cl | Cl | —OCH₂CH₂CH₂— | |
| H | Cl | Br | —OCH₂CH₂CH₂— | |
| F | Cl | Br | —OCH₂CH₂CH₂— | |
| H | Cl | CH₃ | —OCH₂CH₂CH₂— | |
| F | Cl | CH₃ | —OCH₂CH₂CH₂— | |
| H | Cl | CH₂CH₃ | —OCH₂CH₂CH₂— | |
| F | Cl | CH₂CH₃ | —OCH₂CH₂CH₂— | |
| H | Cl | H | —CH₂OCH₂CH₂— | |
| F | Cl | H | —CH₂OCH₂CH₂— | |
| H | Cl | Cl | —CH₂OCH₂CH₂— | |
| F | Cl | Cl | —CH₂OCH₂CH₂— | |
| H | Cl | Br | —CH₂OCH₂CH₂— | |
| F | Cl | Br | —CH₂OCH₂CH₂— | |
| H | Cl | CH₃ | —CH₂OCH₂CH₂— | |
| F | Cl | CH₃ | —CH₂OCH₂CH₂— | |
| H | Cl | CH₂CH₃ | —CH₂OCH₂CH₂— | |
| F | Cl | CH₂CH₃ | —CH₂OCH₂CH₂— | |
| H | Cl | H | —OCH₂CH₂CH₂CH₂— | |
| F | Cl | H | —OCH₂CH₂CH₂CH₂— | |
| H | Cl | Cl | —OCH₂CH₂CH₂CH₂— | |
| F | Cl | Cl | —OCH₂CH₂CH₂CH₂— | |

TABLE I-continued

| R¹ | R² | R³ | R⁴ | R⁵ |
|---|---|---|---|---|
| H | Cl | Br | —OCH₂CH₂CH₂CH₂— | |
| F | Cl | Br | —OCH₂CH₂CH₂CH₂— | |
| H | Cl | CH₃ | —OCH₂CH₂CH₂CH₂— | |
| F | Cl | CH₃ | —OCH₂CH₂CH₂CH₂— | |
| H | Cl | CH₂CH₃ | —OCH₂CH₂CH₂CH₂— | |
| F | Cl | CH₂CH₃ | —OCH₂CH₂CH₂CH₂— | |
| H | Cl | H | —CH₂OCH₂CH₂CH₂— | |
| F | Cl | H | —CH₂OCH₂CH₂CH₂— | |
| H | Cl | Cl | —CH₂OCH₂CH₂CH₂— | |
| F | Cl | Cl | —CH₂OCH₂CH₂CH₂— | |
| H | Cl | Br | —CH₂OCH₂CH₂CH₂— | |
| F | Cl | Br | —CH₂OCH₂CH₂CH₂— | |
| H | Cl | CH₃ | —CH₂OCH₂CH₂CH₂— | |
| F | Cl | CH₃ | —CH₂OCH₂CH₂CH₂— | |
| H | Cl | CH₂CH₃ | —CH₂OCH₂CH₂CH₂— | |
| F | Cl | CH₂CH₃ | —CH₂OCH₂CH₂CH₂— | |
| H | Cl | H | —CH₂CH₂OCH₂CH₂— | |
| F | Cl | H | —CH₂CH₂OCH₂CH₂— | |
| H | Cl | Cl | —CH₂CH₂OCH₂CH₂— | |
| F | Cl | Cl | —CH₂CH₂OCH₂CH₂— | |
| H | Cl | Br | —CH₂CH₂OCH₂CH₂— | |
| F | Cl | Br | —CH₂CH₂OCH₂CH₂— | |
| H | Cl | CH₃ | —CH₂CH₂OCH₂CH₂— | |
| F | Cl | CH₃ | —CH₂CH₂OCH₂CH₂— | |
| H | Cl | CH₂CH₃ | —CH₂CH₂OCH₂CH₂— | |
| F | Cl | CH₂CH₃ | —CH₂CH₂OCH₂CH₂— | |
| H | F | Cl | H | CH₃ |
| H | F | Br | H | CH₃ |
| H | F | CH₃ | H | CH₃ |
| H | F | Cl | H | CH₂CH=CH₂ |
| H | F | Br | H | CH₂CH=CH₂ |
| H | F | CH₃ | H | CH₂CH=CH₂ |
| H | F | Cl | H | CH₂C≡CH |
| H | F | Br | H | CH₂C≡CH |
| H | F | CH₃ | H | CH₂C≡CH |
| H | F | Cl | H | (CH₂)₂OCH₃ |
| H | F | Br | H | (CH₂)₂OCH₃ |
| H | F | CH₃ | H | (CH₂)₂OCH₃ |
| H | F | Cl | H | OCH₂CH₃ |
| H | F | Br | H | OCH₂CH₃ |
| H | F | CH₃ | H | OCH₂CH₃ |
| H | F | Cl | H | OCH₂CH=CH₂ |
| H | F | Br | H | OCH₂CH=CH₂ |
| H | F | CH₃ | H | OCH₂CH=CH₂ |
| H | F | Cl | H | OCH₂C≡CH |
| H | F | Br | H | OCH₂C≡CH |
| H | F | CH₃ | H | OCH₂C≡CH |

TABLE II

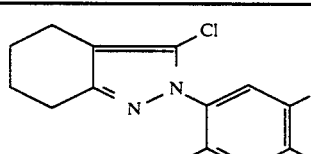

Ib

| R¹ | R² | R³ | R⁶ |
|---|---|---|---|
| H | Cl | H | H |
| F | Cl | H | H |
| H | Br | H | H |
| F | Br | H | H |
| H | Cl | Cl | H |
| F | Cl | Cl | H |
| H | Br | Cl | H |
| F | Br | Cl | H |
| H | Cl | Br | H |
| F | Cl | Br | H |
| H | Br | Br | H |
| F | Br | Br | H |
| H | Cl | CH₃ | H |
| F | Cl | CH₃ | H |
| H | Br | CH₃ | H |
| F | Br | CH₃ | H |
| H | Cl | CH₂CH₃ | H |
| F | Cl | CH₂CH₃ | H |
| H | Br | CH₂CH₃ | H |
| F | Br | CH₂CH₃ | H |
| H | Cl | H | CH₃ |

TABLE II-continued

Structure Ib: tetrahydroindazole with Cl at 3-position, N-linked to phenyl ring bearing R¹, R², and a CH=C(R³)CO₂R⁶ group.

| R¹ | R² | R³ | R⁶ |
|---|---|---|---|
| F | Cl | H | CH₃ |
| H | Br | H | CH₃ |
| F | Br | H | CH₃ |
| H | Cl | Cl | CH₃ |
| F | Cl | Cl | CH₃ |
| H | Br | Cl | CH₃ |
| F | Br | Cl | CH₃ |
| H | Cl | Br | CH₃ |
| F | Cl | Br | CH₃ |
| H | Br | Br | CH₃ |
| F | Br | Br | CH₃ |
| H | Cl | CH₃ | CH₃ |
| F | Cl | CH₃ | CH₃ |
| H | Br | CH₃ | CH₃ |
| F | Br | CH₃ | CH₃ |
| H | Cl | CH₂CH₃ | CH₃ |
| F | Cl | CH₂CH₃ | CH₃ |
| H | Br | CH₂CH₃ | CH₃ |
| F | Br | CH₂CH₃ | CH₃ |
| H | Cl | H | CH₂CH₃ |
| F | Cl | H | CH₂CH₃ |
| H | Br | H | CH₂CH₃ |
| F | Br | H | CH₂CH₃ |
| H | Cl | Cl | CH₂CH₃ |
| F | Cl | Cl | CH₂CH₃ |
| H | Br | Cl | CH₂CH₃ |
| F | Br | Cl | CH₂CH₃ |
| H | Cl | Br | CH₂CH₃ |
| F | Cl | Br | CH₂CH₃ |
| H | Br | Br | CH₂CH₃ |
| F | Br | Br | CH₂CH₃ |
| H | Cl | CH₃ | CH₂CH₃ |
| F | Cl | CH₃ | CH₂CH₃ |
| H | Br | CH₃ | CH₂CH₃ |
| F | Br | CH₃ | CH₂CH₃ |
| H | Cl | CH₂CH₃ | CH₂CH₃ |
| F | Cl | CH₂CH₃ | CH₂CH₃ |
| H | Br | CH₂CH₃ | CH₂CH₃ |
| F | Br | CH₂CH₃ | CH₂CH₃ |
| H | Cl | H | (CH₂)₂CH₃ |
| F | Cl | H | (CH₂)₂CH₃ |
| H | Cl | Cl | (CH₂)₂CH₃ |
| F | Cl | Cl | (CH₂)₂CH₃ |
| H | Cl | Br | (CH₂)₂CH₃ |
| F | Cl | Br | (CH₂)₂CH₃ |
| H | Cl | CH₃ | (CH₂)₂CH₃ |
| F | Cl | CH₃ | (CH₂)₂CH₃ |
| H | Cl | CH₂CH₃ | (CH₂)₂CH₃ |
| F | Cl | CH₂CH₃ | (CH₂)₂CH₃ |
| H | Cl | H | CH(CH₃)₂ |
| F | Cl | H | CH(CH₃)₂ |
| H | Cl | Cl | CH(CH₃)₂ |
| F | Cl | Cl | CH(CH₃)₂ |
| H | Cl | Br | CH(CH₃)₂ |
| F | Cl | Br | CH(CH₃)₂ |
| H | Cl | CH₃ | CH(CH₃)₂ |
| F | Cl | CH₃ | CH(CH₃)₂ |
| H | Cl | CH₂CH₃ | CH(CH₃)₂ |
| F | Cl | CH₂CH₃ | CH(CH₃)₂ |
| H | Cl | H | (CH₂)₃CH₃ |
| F | Cl | H | (CH₂)₃CH₃ |
| H | Cl | Cl | (CH₂)₃CH₃ |
| F | Cl | Cl | (CH₂)₃CH₃ |
| H | Cl | Br | (CH₂)₃CH₃ |
| F | Cl | Br | (CH₂)₃CH₃ |
| H | Cl | CH₃ | (CH₂)₃CH₃ |
| F | Cl | CH₃ | (CH₂)₃CH₃ |
| H | Cl | CH₂CH₃ | (CH₂)₃CH₃ |
| F | Cl | CH₂CH₃ | (CH₂)₃CH₃ |
| H | Cl | H | CH₂CH(CH₃)₂ |
| F | Cl | H | CH₂CH(CH₃)₂ |
| H | Cl | Cl | CH₂CH(CH₃)₂ |
| F | Cl | Cl | CH₂CH(CH₃)₂ |
| H | Cl | Br | CH₂CH(CH₃)₂ |
| F | Cl | Br | CH₂CH(CH₃)₂ |
| H | Cl | CH₃ | CH₂CH(CH₃)₂ |
| F | Cl | CH₃ | CH₂CH(CH₃)₂ |
| H | Cl | CH₂CH₃ | CH₂CH(CH₃)₂ |
| F | Cl | CH₂CH₃ | CH₂CH(CH₃)₂ |
| H | Cl | H | (CH₂)₄CH₃ |
| F | Cl | H | (CH₂)₄CH₃ |
| H | Cl | Cl | (CH₂)₄CH₃ |
| F | Cl | Cl | (CH₂)₄CH₃ |
| H | Cl | Br | (CH₂)₄CH₃ |
| F | Cl | Br | (CH₂)₄CH₃ |
| H | Cl | CH₃ | (CH₂)₄CH₃ |
| F | Cl | CH₃ | (CH₂)₄CH₃ |
| H | Cl | CH₂CH₃ | (CH₂)₄CH₃ |
| F | Cl | CH₂CH₃ | (CH₂)₄CH₃ |
| H | Cl | H | (CH₂)₂CH(CH₃)₂ |
| F | Cl | H | (CH₂)₂CH(CH₃)₂ |
| H | Cl | Cl | (CH₂)₂CH(CH₃)₂ |
| F | Cl | Cl | (CH₂)₂CH(CH₃)₂ |
| H | Cl | Br | (CH₂)₂CH(CH₃)₂ |
| F | Cl | Br | (CH₂)₂CH(CH₃)₂ |
| H | Cl | CH₃ | (CH₂)₂CH(CH₃)₂ |
| F | Cl | CH₃ | (CH₂)₂CH(CH₃)₂ |
| H | Cl | CH₂CH₃ | (CH₂)₂CH(CH₃)₂ |
| F | Cl | CH₂CH₃ | (CH₂)₂CH(CH₃)₂ |
| H | Cl | H | (CH₂)₂OCH₃ |
| F | Cl | H | (CH₂)₂OCH₃ |
| H | Cl | Cl | (CH₂)₂OCH₃ |
| F | Cl | Cl | (CH₂)₂OCH₃ |
| H | Cl | Br | (CH₂)₂OCH₃ |
| F | Cl | Br | (CH₂)₂OCH₃ |
| H | Cl | CH₃ | (CH₂)₂OCH₃ |
| F | Cl | CH₃ | (CH₂)₂OCH₃ |
| H | Cl | CH₂CH₃ | (CH₂)₂OCH₃ |
| F | Cl | CH₂CH₃ | (CH₂)₂OCH₃ |
| H | Cl | H | CH(CH₃)CH₂OCH₃ |
| F | Cl | H | CH(CH₃)CH₂OCH₃ |
| H | Cl | Cl | CH(CH₃)CH₂OCH₃ |
| F | Cl | Cl | CH(CH₃)CH₂OCH₃ |
| H | Cl | Br | CH(CH₃)CH₂OCH₃ |
| F | Cl | Br | CH(CH₃)CH₂OCH₃ |
| H | Cl | CH₃ | CH(CH₃)CH₂OCH₃ |
| F | Cl | CH₃ | CH(CH₃)CH₂OCH₃ |
| H | Cl | CH₂CH₃ | CH(CH₃)CH₂OCH₃ |
| F | Cl | CH₂CH₃ | CH(CH₃)CH₂OCH₃ |
| H | Cl | H | CH₂CH=CH₂ |
| F | Cl | H | CH₂CH=CH₂ |
| H | Cl | Cl | CH₂CH=CH₂ |
| F | Cl | Cl | CH₂CH=CH₂ |
| H | Cl | Br | CH₂CH=CH₂ |
| F | Cl | Br | CH₂CH=CH₂ |
| H | Cl | CH₃ | CH₂CH=CH₂ |
| F | Cl | CH₃ | CH₂CH=CH₂ |
| H | Cl | CH₂CH₃ | CH₂CH=CH₂ |
| F | Cl | CH₂CH₃ | CH₂CH=CH₂ |
| H | Cl | H | CH₂CH=CHCH₃ |
| F | Cl | H | CH₂CH=CHCH₃ |
| H | Cl | Cl | CH₂CH=CHCH₃ |
| F | Cl | Cl | CH₂CH=CHCH₃ |
| H | Cl | Br | CH₂CH=CHCH₃ |
| F | Cl | Br | CH₂CH=CHCH₃ |
| H | Cl | CH₃ | CH₂CH=CHCH₃ |
| F | Cl | CH₃ | CH₂CH=CHCH₃ |
| H | Cl | CH₂CH₃ | CH₂CH=CHCH₃ |
| F | Cl | CH₂CH₃ | CH₂CH=CHCH₃ |
| H | Cl | H | CH₂C≡CH |
| F | Cl | H | CH₂C≡CH |
| H | Cl | Cl | CH₂C≡CH |
| F | Cl | Cl | CH₂C≡CH |
| H | Cl | Br | CH₂C≡CH |

TABLE II-continued

Ib: tetrahydroindazole with Cl at 3-position, N-N linked to phenyl ring bearing R¹, R², and CH=C(R³)(CO₂R⁶) substituent

| R¹ | R² | R³ | R⁶ |
|---|---|---|---|
| F | Cl | Br | CH₂C≡CH |
| H | Cl | CH₃ | CH₂C≡CH |
| F | Cl | CH₃ | CH₂C≡CH |
| H | Cl | CH₂CH₃ | CH₂C≡CH |
| F | Cl | CH₂CH₃ | CH₂C≡CH |
| H | Cl | H | CH₂C≡CCH₃ |
| F | Cl | H | CH₂C≡CCH₃ |
| H | Cl | Cl | CH₂C≡CCH₃ |
| F | Cl | Cl | CH₂C≡CCH₃ |
| H | Cl | Br | CH₂C≡CCH₃ |
| F | Cl | Br | CH₂C≡CCH₃ |
| H | Cl | CH₃ | CH₂C≡CCH₃ |
| F | Cl | CH₃ | CH₂C≡CCH₃ |
| H | Cl | CH₂CH₃ | CH₂C≡CCH₃ |
| F | Cl | CH₂CH₃ | CH₂C≡CCH₃ |
| H | Cl | H | CH₂Ph |
| F | Cl | H | CH₂Ph |
| H | Cl | Cl | CH₂Ph |
| F | Cl | Cl | CH₂Ph |
| H | Cl | Br | CH₂Ph |
| F | Cl | Br | CH₂Ph |
| H | Cl | CH₃ | CH₂Ph |
| F | Cl | CH₃ | CH₂Ph |
| H | Cl | CH₂CH₃ | CH₂Ph |
| F | Cl | CH₂CH₃ | CH₂Ph |
| H | F | Cl | CH₃ |
| H | F | Br | CH₃ |
| H | F | CH₃ | CH₃ |
| H | F | Cl | CH₂CH₃ |
| H | F | Br | CH₂CH₃ |
| H | F | CH₃ | CH₂CH₃ |
| H | F | Cl | (CH₂)₂CH₃ |
| H | F | Br | (CH₂)₂CH₃ |
| H | F | CH₃ | (CH₂)₂CH₃ |
| H | F | Cl | CH(CH₃)₂ |
| H | F | Br | CH(CH₃)₂ |
| H | F | CH₃ | CH(CH₃)₂ |
| H | F | Cl | (CH₂)₃CH₃ |
| H | F | Br | (CH₂)₃CH₃ |
| H | F | CH₃ | (CH₂)₃CH₃ |
| H | F | Cl | CH₂CH(CH₃)₂ |
| H | F | Br | CH₂CH(CH₃)₂ |
| H | F | CH₃ | CH₂CH(CH₃)₂ |
| H | F | Cl | (CH₂)₄CH₃ |
| H | F | Br | (CH₂)₄CH₃ |
| H | F | CH₃ | (CH₂)₄CH₃ |
| H | F | Cl | (CH₂)₂CH(CH₃)₂ |
| H | F | Br | (CH₂)₂CH(CH₃)₂ |
| H | F | CH₃ | (CH₂)₂CH(CH₃)₂ |
| H | F | Cl | (CH₂)₂OCH₃ |
| H | F | Br | (CH₂)₂OCH₃ |
| H | F | CH₃ | (CH₂)₂OCH₃ |
| H | F | Cl | CH(CH₃)CH₂OCH₃ |
| H | F | Br | CH(CH₃)CH₂OCH₃ |
| H | F | CH₃ | CH(CH₃)CH₂OCH₃ |
| H | F | Cl | CH₂CH=CH₂ |
| H | F | Br | CH₂CH=CH₂ |
| H | F | CH₃ | CH₂CH=CH₂ |
| H | F | Cl | CH₂CH=CHCH₃ |
| H | F | Br | CH₂CH=CHCH₃ |
| H | F | CH₃ | CH₂CH=CHCH₃ |
| H | F | Cl | CH₂CH≡CH |
| H | F | Br | CH₂CH≡CH |
| H | F | CH₃ | CH₂CH≡CH |
| H | F | Cl | CH₂C≡CCH₃ |
| H | F | Br | CH₂C≡CCH₃ |
| H | F | CH₃ | CH₂C≡CCH₃ |
| H | F | Cl | CH₂Ph |
| H | F | Br | CH₂Ph |
| H | F | CH₃ | CH₂Ph |

The N-phenyltetrahydroindazole derivatives Ia and Ib, and herbicidal agents containing them, may be applied for instance in the form of directly sprayable solutions, powders, suspensions (including high-percentage aqueous, oily or other suspension), dispersion emulsions, oil dispersion, pastes, dusts, broadcasting agents, or granules by spraying, atomizing, dusting, broadcasting or watering. The forms of application depend entirely on the purpose for which the agents are being used, but they must ensure as a fine a distribution of the active ingredients according to the invention as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as toluene, xylene, paraffin, tetrahydronaphthalene, alkylated naphthalenes and their derivatives, methanol, ethanolpropanol, butanol, cyclohexanol, cyclohexanone, chlorobenzene, isophorone, etc., and strongly polar solvents such as N,N-dimethylformamide, dimethyl sulfoxide, N-methylpyrrolidone, water, etc. are suitable.

Aqueous formulations may be prepared from emulsion concentrates, pastes, oil dispersions, wettable powders or water-dispersible granules by adding water. To prepare emulsions, pastes and oil dispersion the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are alkali metal, alkaline earth metal and ammonium salts of aromatic sulfonic acids, e.g., ligninsulfonic acid, phenolsulfonic acid, naphthalenesulfonic acid and dibutylnaphthalenesulfonic acid, and of fatty acids, alkyl and alkylaryl sulfonates, and alkyl, lauryl ether and fatty alcohol sulfates, and salts of sulfated hexadecanols, heptadecanols, and octadecanols, salts of fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin-sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acids, silica gels, silicates, talc, kaolin, attapulgus clay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain meals, bark meal, wood meal, and nutshell meal, cellulosic powders, etc.

The formulations contain from 0.1 to 95, and preferably 0.5 to 90, % by weight of active ingredient.

Examples of formulations are as follows:

I. 90 parts by weight of compound no. 1.001 is mixed with 10 parts by weight of N-methyl-alpha-pyrrolidone. A mixture is obtained which is suitable for application in the form of very fine drops.

II. 20 parts by weight of compound no. 1.001 is dissolved in a mizture consisting of 80 parts by weight of xylene, 10 parts by weight of adduct of 8 to 10 moles of ethylene oxide and 1 mole of oleic acid-N-monoethanolamide, 5 parts by weight of the calcium slat of dodecylbenzenesulfonic acid, and 5 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

III. 20 parts by weight of compound no. 1.001 is dissolved in a mixture consisting of 40 parts by weight of cyclohexanone, 30 parts by weight of isobutanol, 20 parts by weight of the adduct of 67 moles of ethylene oxide and 1 mole of isooctylphenol, and 10 parts by weight of the adduct of 40 moles of ethylene oxide and 1 mole of castor oil. By pouring the solution into 100,000 parts by weight of water and finely distributing it therein, an aqueous dispersion is obtained containing 0.02% by weight of the active ingredient.

IV. 20 parts by weight of compound no. 1.002 is dissolved in a mixture consisting of 25 parts by weight of cyclohexanone, 65 parts by weight of a mineral oil fraction having a boiling point between 210 and 280° C., and 10 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

V. 20 parts by weight of compound no. 1.001 is well mixed with 3 parts by weight of the sodium salt of diisobutylnaphthalene-alpha-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquor is obtained containing 0.1% by weight of the active ingredient.

VI. 3 parts by weight of compound no. 1.002 is intimately mixed with 97 parts by weight of particulate kaolin. A dust is obtained containing 3% by weight of the active ingredient.

VII. 30 parts by weight of compound no. 1.002 is intimately mixed with a mixture consisting of 92 parts by weight of powdered silica gel and 8 parts by weight of paraffin oil which as been sprayed onto the surface of this silica gel. A formulation of the active ingredient is obtained having good adherence.

VIII. 20 parts by weight of compound no. 1.002 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

The active ingredients or the herbicidal agents containing them may be applied pre- or postemergence. If certain crop plants tolerate the active ingredients less well, application techniques may be used in which the herbicidal agents are sprayed from suitable equipment in such a manner that the leaves of sensitive crop plants are if possible not touched, and the agents reach the soil or the unwanted plants growing beneath the crop plants (post-directed, lay-by treatment).

The application rates depend on the object to be achieved, the time of the year, the plants to be combated and their growth stage, and are from 0.001 to 3.0, preferably 0.01 to 1.0, kg of active ingredient per hectare. are.

In view of the numerous application methods possible, the compounds according to the invention may be used in a large number of crops. Those which follow are given by way of example:

| Botanical name | Common name |
| --- | --- |
| Allium cepa | onions |
| Ananas comosus | pineapples |
| Arachis hypogaea | peanuts (groundnuts) |
| Asparagus officinalis | asparagus |
| Avena sativa | oats |
| Beta vulgaris spp. altissima | sugarbeets |
| Beta vulgaris spp. rapa | fodder beets |
| Beta vulgaris spp. esculenta | table beets, red beets |
| Brassica napus var. napus | rapeseed |
| Brassica napus var. napobrassica | swedes |
| Brassica napus var. rapa | turnips |
| Brassica rapa var. silvestris | |
| Camellia sinensis | tea plants |
| Carthamus tinctorius | safflower |
| Carya illinoinensis | pecan trees |
| Citrus limon | lemons |
| Citrus maxima | grapefruits |
| Citrus reticulata | mandarins |
| Citrus sinensis | orange trees |
| Coffea arabica (Coffea canephora, Coffea liberica) | coffee plants |
| Cucumis melo | melons |
| Cucumis sativus | cucumbers |
| Cynodon dactylon | Bermudagrass |
| Daucus carota | carrots |
| Elais guineensis | oil palms |
| Fragaria vesca | strawberries |
| Glycine max | soybeans |
| Gossypium hirsutum (Gossypium arboreum, Gossypium herbaceum, Gossypium vitifolium) | cotton |
| Helianthus annuus | sunflowers |
| Helianthus tuberosus | Jerusalem artichoke |
| Hevea brasiliensis | rubber plants |
| Hordeum vulgare | barley |
| Humulus lupulus | hops |
| Ipomoea batatas | sweet potatoes |
| Juglans regia | walnut trees |
| Lactuca sativa | lettuce |
| Lens culinaris | lentils |
| Linum usitatissimum | flax |
| Lycopersicon lycopersicum | tomatoes |
| Malus spp. | apple trees |
| Manihot esculenta | cassava |
| Medicago sativa | alfalfa (lucerne) |
| Mentha piperita | peppermint |
| Musa spp. | banana plants |
| Nicotiana tabacum (N. rustica) | tobacco |
| Olea europaea | olive trees |
| Oryza sativa | rice |
| Panicum miliaceum | millet |
| Phaseolus lunatus | limabeans |
| Phaseolus mungo | mungbeans |
| Phaseolus vulgaris | snapbeans, green beans, dry beans |
| Pennisetum glaucum | pearl millet |
| Petroselinum crispum spp. tuberosum | parsley |
| Picea abies | Norway spruce |

-continued

| Botanical name | Common name |
| --- | --- |
| Abies alba | fir trees |
| Pinus spp. | pine trees |
| Pisum sativum | English peas |
| Prunus avium | cherry trees |
| Prunus domestica | plum trees |
| Prunus dulcis | almond trees |
| Prunus persica | peach trees |
| Pyrus communis | pear trees |
| Ribes sylvestre | redcurrants |
| Ribes uva-crispa | gooseberries |
| Ricinus communis | castor-oil plants |
| Saccharum officinarum | sugar cane |
| Secale cereale | rye |
| Sesamum indicum | sesame |
| Solanum tuberosum | Irish potatoes |
| Sorghum bicolor (s. vulgare) | sorghum |
| Sorghum dochna | sorgo |
| Spinacia oleracea | spinach |
| Theobroma cacao | cacao plants |
| Trifolium pratense | red clover |
| Triticum aestivum | wheat |
| Vaccinium corymbosum | blueberries |
| Vaccinium vitis-idaea | cranberries |
| Vicia faba | tick beans |
| Vigna sinensis (V. unguiculata) | cow peas |
| Vitis vinifera | grapes |
| Zea mays | Indian corn, sweet corn, maize |

To increase the spectrum of action and to achieve synergistic effects, the N-phenyltetrahydroindazole derivatives of the formula Ia and Ib may be mixed with each other, or mixed and applied together with numerous representatives of other herbicidal or growth-regulating active ingredient groups. Examples of suitable components are diazines, 4H-3,1-benzoxazine derivatives, benzothiadiazinones, 2,6-dinitroanilines, N-phenylcarbamates, thiolcarbamates, halocarboxylic acids, triazines, amides, ureas, diphenyl ethers, triazinones, uracils, benzofuran derivatives, quinolinecarboxylic acids, (heterto)-aryloxyphenoxypropionic acid derivatives (salts, esters, amides), etc.

It may also be useful to apply the novel compounds of the formulae Ia and Ib, either alone or in combination with other herbicides, in admixture with other crop protection agents, e.g., agents for combating pests or phytopathogenic fungi or bacteria. The compounds may also be mixed with solutions of mineral salts used to remedy nutritional or trace element deficiencies. Non-phytotoxic oils and oil concentrates may also be added.

SYNTHESIS EXAMPLES

The directions given in the synthesis examples which follow were used, with the corresponding starting materials, to obtain further compounds Ia and Ib. These compounds are listed in the tables below with their physical data.

EXAMPLE 1

Preparation of E/Z-3-chloro-2-[3-(2-methoxycarbonylprop-1-enyl)-4-chlorophenyl]-4,5,6,7-tetrahydroindazole

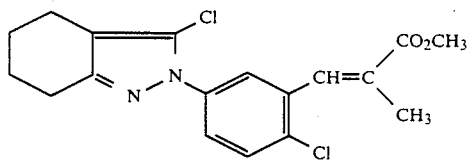

(a) At 0 to 5° C., a solution of 5 g (72 mmol) of sodium nitrite and 14 ml of water was slowly added to a mixture of 1.4 g (72 mmol) of 2-chloro-5-amine-α-methylcinnamic acid, 35 ml of acetic acid and 21 ml of concentrated hydrochloric acid. After the mixture had been stirred for 30 minutes at 5° C., first 150 ml of concentrated hydrochloric acid and then 32.4 g (143 mmol) of $SnCl_2 \times 2H_2O$ in 30 ml of concentrated HCl were dripped in. The reaction mixture obtained was stirred for 12 hours at room temperature and the precipitate which formed was isolated. E/Z-3-(2-hydroxycarbonylprop-1-enyl)-4-chlorophenylhydrazine was obtained in quantitative yield (oil).

(b) 11.3 g (50 mmol) of the phenylhydrazine from (a) was added to a solution 9.35 g (55mmol) of ethyl cyclohexanone-2-carboxylate, 100 ml of glacial acetic acid, 4.1 g (50 mmol) of sodium acetate and 10 ml of water. After the mixture had been kept for 6 hours at the boiling temperature and cooled to 25° C., the solid which had precipitated was isolated. There was obtained 5.8 g (35%) of E/Z-2-[3-(2-hydroxycarbonylprop-1-enyl)-4-chlorophenyl]-1,2,4,5,6,7-hexahydro-3H-indazol-3-one (m.p. 278° C.).

(c) At 25° C., 1.29 g (84 mmol) of phosphorus oxychloride was added to a mixture of 5.6 g (167 mmol) of the indazolone from (b) and 850 mg of dimethylformamide. The mixture was stirred for 30 minutes at 25° C., and then for 1 hour at the boiling temperature. The excess phosphorus oxychloride was then distilled off, and 54 ml of methanol was added, with 'cooling, to the residue at 25° C., and after 15 minutes 5.3 g (67 mmol) of pyridine was added. The mixture was stirred for 12 hours at 25° C. and then concentrated, and the residue was taken up in 100 ml of ethyl acetate, washed and dried. After chromatographic purification, there was obtained 3.3 g (b 53%) of the title compound as an oil (active ingredient example 1.001).

TABLE 1

| Active ingr. no. | $R^1$ | $R^2$ | $R^3$ | Z | Phys data [mp (°C.); IR (cm$^{-1}$); NMR (ppm)] |
| --- | --- | --- | --- | --- | --- |
| 1.001 | H | Cl | CH$_3$ | OCH$_3$ | NMR: 2.05(s); 3.85(s) |
| 1.002 | H | Cl | CH$_3$ | OCH$_2$CH$_3$ | NMR: 2.05(s); 4.35(q) |
| 1.003 | H | Cl | Br | OCH$_3$ | mp.: 83–85 |
| 1.004 | H | Cl | Br | OCH$_2$CH$_3$ | mp.: 70–71 |
| 1.005 | H | Cl | Cl | OCH$_2$CH$_3$ | mp.: 57–58 |
| 1.006 | H | Cl | Cl | OCH$_3$ | mp.: 71–72 |
| 1.007 | H | Cl | Br | OC(CH$_3$)$_3$ | IR: 2936, 1723, 1156, 1006 |
| 1.008 | H | Cl | Cl | OC(CH$_3$)$_3$ | IR: 2936, 1726, 1158, 1016 |
| 1.009 | H | Cl | Cl | OCH(CH$_3$)$_2$ | mp.: 64–65 |
| 1.010 | H | Cl | Br | OCH(CH$_3$)$_2$ | mp.: 84–85 |
| 1.011 | H | Cl | I | OCH$_3$ | mp.: 91–92 |

USE EXAMPLES

The herbicidal action of the N-(phenyl)-tetrahydroindazole derivatives Ia and Ib on the growth of the test plants is illustrated in the following greenhouse experiments.

The vessels employed were plastic flowerpots having a volume of 300 cm³ and filled with a sandy loam containing about 3.0% humus. The seeds of the test plants were sown separately, according to species.

For the postemergence treatment, either plants sown directly in the pots and grown there were used, or plants which were cultivated separately as seedlings and were transplanted to the vessels a few days before treatment.

Depending on growth form, the plants were grown to a height of 3 to 15 cm before being treated with the active ingredients, which were suspended or emulsified in water and sprayed through finely distributing nozzles. The application rate for postemergence treatment was 0.06 kg/ha.

The pots were set up in the greenhouse, species from warner climates in warner areas (20 to 35° C.) and species from moderate climates at 10 to 20° C. The experiments were run for from 2 to 4 weeks. During this time the plants were tended and their reactions to the various treatments assessed.

The assessment scale was 0 to 100, 100 denoting nonemergence or complete destruction of at least the visible plant parts, and 0 denoting no damage or normal growth.

The plants used in the experiments were Abutilon theophrasti, Amaranthus Retroflexus, Chenopodium album, Solanum nigrum and Triticum aestivum.

Compounds 1.001 and 1.002, employed postemergence at a rate of 0.06 kg/ha, combated unwanted broadleaved plants excellently without any appreciable damage being caused to the crop plant wheat.

We claim:

1. N-Phenyltetrahydroindazole derivatives of the formulae Ia and Ib

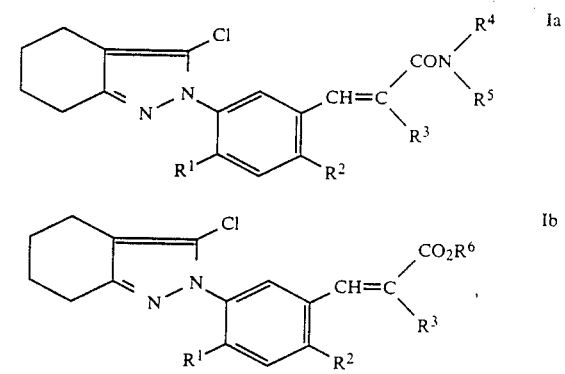

where
R¹ is hydrogen or fluorine,
R² is halogen,
R³ is hydrogen, halogen or a $C_1$–$C_4$-alkyl,
R⁴, R⁵ are hydrogen, $C_1$–$C_8$-alkyl, $C_2$14 $C_4$-alkyl which carries a hydroxyl, $C_1$–$C_4$-alkoxy or $C_1$–$C_4$-alkylthio group, $C_1$–$C_6$-alkoxy, $C_3$–$C_6$-alkenyl, $C_3$–$C_6$-alkynyl, $C_3$–$C_6$-alkenyloxy or $C_3$–$C_6$-alkynyloxy, or together with the nitrogen atom form a 5- or 6-membered aliphatic ring in which a methylene group may be replaced by an oxygen atom, and
R⁶ is hydrogen, $C_1$–$C_6$-alkyl which is unsubstituted or substituted by one or two $C_1$–$C_4$-alkoxy groups, or is $C_3$–$C_6$-alkenyl, $C_3$–$C_6$-aklynyl or benzyl.

2. A herbicidal agent which comprises an N-phenyl-tetrahydroindazole derivative of the formulae Ia or Ib, or a mixture of Ia and Ib, as set forth in claim 1, and inert additives.

3. A process for combating the growth of unwanted plants, wherein the unwanted plants or their habitat are treated with a herbicidally effective amount of an N-phenyltetrahydroindazole derivative Ia or Ib, or a mixture of Ia and Ib, as set forth in claim 1.

* * * * *

UNITED STATES PATENT AND TRADEMARK OFFICE
CERTIFICATE OF CORRECTION

PATENT NO. : 4,990,174

DATED : FEB. 5, 1991

INVENTOR(S) : RUEB et al.

It is certified that error appears in the above-identified patent and that said Letters Patent is hereby corrected as shown below:

on the cover sheet, in the abstract, before formula Ia insert:

--N-Phenyltetrahydroindazole derivatives of the general formulae Ia and Ib-- in claim 1, column 24, line 21: "$R^1$" should read --$R^4$-- in claim 1, column 24, line 21: "$C_2 14C_4$" should read --$C_2$-$C_4$--

Signed and Sealed this

Sixteenth Day of November, 1993

Attest:

BRUCE LEHMAN

Attesting Officer     Commissioner of Patents and Trademarks